(12) United States Patent
Murakami et al.

(10) Patent No.: US 11,090,419 B2
(45) Date of Patent: Aug. 17, 2021

(54) BLOOD PURIFICATION APPARATUS

(71) Applicant: Nikkiso Company Limited, Tokyo (JP)

(72) Inventors: Tomoya Murakami, Shizuoka (JP); Kunihiko Akita, Shizuoka (JP); Masahiro Toyoda, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 377 days.

(21) Appl. No.: 15/055,219

(22) Filed: Feb. 26, 2016

(65) Prior Publication Data

US 2016/0175508 A1 Jun. 23, 2016

Related U.S. Application Data

(63) Continuation of application No. PCT/JP2014/072924, filed on Sep. 1, 2014.

(30) Foreign Application Priority Data

Sep. 2, 2013 (JP) .............................. JP2013-181219

(51) Int. Cl.
*A61M 1/16* (2006.01)
*G16H 20/40* (2018.01)

(52) U.S. Cl.
CPC ........ *A61M 1/1609* (2014.02); *A61M 1/1603* (2014.02); *A61M 1/1613* (2014.02); *A61M 2205/3306* (2013.01); *G16H 20/40* (2018.01)

(58) Field of Classification Search
CPC .............. A61M 1/1603; A61M 1/1609; A61M 1/1613; A61M 1/16; A61M 2205/15;
(Continued)

(56) References Cited

U.S. PATENT DOCUMENTS 3,441,136 A * 4/1969 Wilson, Jr. .............. A61M 1/16
210/103
6,187,199 B1 * 2/2001 Goldau ................... A61M 1/16
210/646
(Continued)

FOREIGN PATENT DOCUMENTS

EP 2005982 A1 12/2008
EP 2163271 A1 3/2010
(Continued)

OTHER PUBLICATIONS

Techwalla, What is the Difference Between a Microcomputer & a Minicomputer?, Apr. 7, 2011 p. 1 (Year: 2011).*
(Continued)

*Primary Examiner* — Bobby Ramdhanie
*Assistant Examiner* — Donovan Bui-Huynh
(74) *Attorney, Agent, or Firm* — Young Basile Hanlon & MacFarlane, P.C.

(57) ABSTRACT

Provided is a blood purification apparatus which can continue to accurately monitor a blood purification treatment state even if treatment conditions are changed during blood purification treatment. The blood purification apparatus can perform real-time monitoring on the blood purification treatment state, based on a concentration change in a discharge solution which is obtained by an arithmetic device. The blood purification apparatus includes a treatment condition change device that sets or changes treatment conditions as requested, and that causes a discharge solution concentration sensor to previously detect concentration of the discharge solution under the respective treatment conditions, and a storage device that stores the concentration of the discharge solution under the respective treatment conditions which is detected by the discharge solution concentration sensor in the treatment condition change device, as a first predetermined value corresponding to the respective treatment con-
(Continued)

ditions. When the treatment conditions are changed during blood purification treatment, the arithmetic device obtains the concentration change in the discharge solution, based on the first predetermined value corresponding to the changed treatment conditions among the first predetermined values stored in the storage device.

19 Claims, 5 Drawing Sheets

(58) Field of Classification Search
CPC .. A61M 2205/3306; A61M 2202/0498; A61M 2205/3317; A61M 2205/3324; A61M 2205/50; A61M 2230/65; A61M 1/1607; A61M 1/361; A61M 1/367; A61M 2205/3313; A61M 2205/52; A61M 1/14; A61M 1/1605; A61M 1/1615; A61M 1/1617; A61M 1/1619; A61M 1/165; A61M 1/1682; A61M 1/1686; A61M 1/1692; A61M 1/3406; A61M 1/3465; A61M 1/3609; A61M 1/3612; A61M 1/3638; A61M 1/3643; A61M 1/3644; A61M 1/3649; A61M 1/365; A61M 1/3652; A61M 1/3653; A61M 1/3658; A61M 2205/3344; A61M 2205/3368; A61M 2205/3379; A61M 2205/502; A61M 2230/20; A61M 1/3639; A61M 1/3656; A61M 1/3659; A61M 1/3661; A61M 2230/04; A61M 2230/42; A61M 1/3655; A43B 13/186; A43B 13/12; A43B 13/125; A43B 13/141; A43B 13/181; A43B 23/027; A43B 5/06; A43B 7/144; A43B 7/1445; A43B 7/149; G01N 21/05; G01N 21/274; G01N 21/59; G01N 2201/0621; G01N 1/4077; G01N 2021/651; G01N 21/65; G01N 2201/062; G01N 2201/0626; G01N 33/491; A61B 5/0059; A61B 5/14546; A61B 5/026; B26F 1/31; C14B 5/00; F04B 1/16; G16H 20/40; H01J 37/31; Y10S 210/929; Y10T 428/24322; Y10T 436/17; Y10T 436/171538; Y10T 436/173845; G06F 19/3481

See application file for complete search history.

(56) References Cited

U.S. PATENT DOCUMENTS

| 6,666,840 | B1* | 12/2003 | Falkvall | A61M 1/16 210/645 |
| 7,488,301 | B2 | 2/2009 | Beden et al. | |
| 8,991,414 | B2 | 3/2015 | Gronau et al. | |
| 2004/0204634 | A1 | 10/2004 | Womble et al. | |
| 2008/0076182 | A1* | 3/2008 | Takahashi | G01N 1/4077 436/63 |
| 2010/0274172 | A1 | 10/2010 | Guenther et al. | |
| 2011/0144459 | A1* | 6/2011 | Akita | A61M 1/16 600/310 |
| 2012/0228226 | A1* | 9/2012 | Castellarnau | A61M 1/16 210/646 |

FOREIGN PATENT DOCUMENTS

| EP | 2292284 A1 | 3/2011 | |
| JP | S60-153138 A | 10/1985 | |
| JP | 2004-016619 A | 1/2004 | |
| JP | 2006-280775 A | 10/2006 | |
| JP | 2007-007435 A | 1/2007 | |
| JP | 2007-167108 A | 7/2007 | |
| JP | 2009-112651 A | 5/2009 | |
| JP | 2009-131412 A | 6/2009 | |
| JP | 2010-273784 A | 12/2009 | |
| JP | 2010-269050 A | 12/2010 | |
| JP | 2011120821 A | 6/2011 | |
| JP | 2011120822 A | 6/2011 | |
| JP | 2011120823 A | 6/2011 | |
| WO | 1999/62574 A1 | 12/1999 | |
| WO | WO-2017165933 A1 * | 10/2017 | F04B 1/16 |

OTHER PUBLICATIONS

Translation of International Search Report, Application No. PCT/JP2014/072924, dated Dec. 2, 2014.

Extended European Search Report, Application No. 13768746.3, dated Oct. 16, 2015.

Extended European Search Report from the European Patent Office for Application No. 14840625.9-1651, dated Mar. 10, 2017.

* cited by examiner

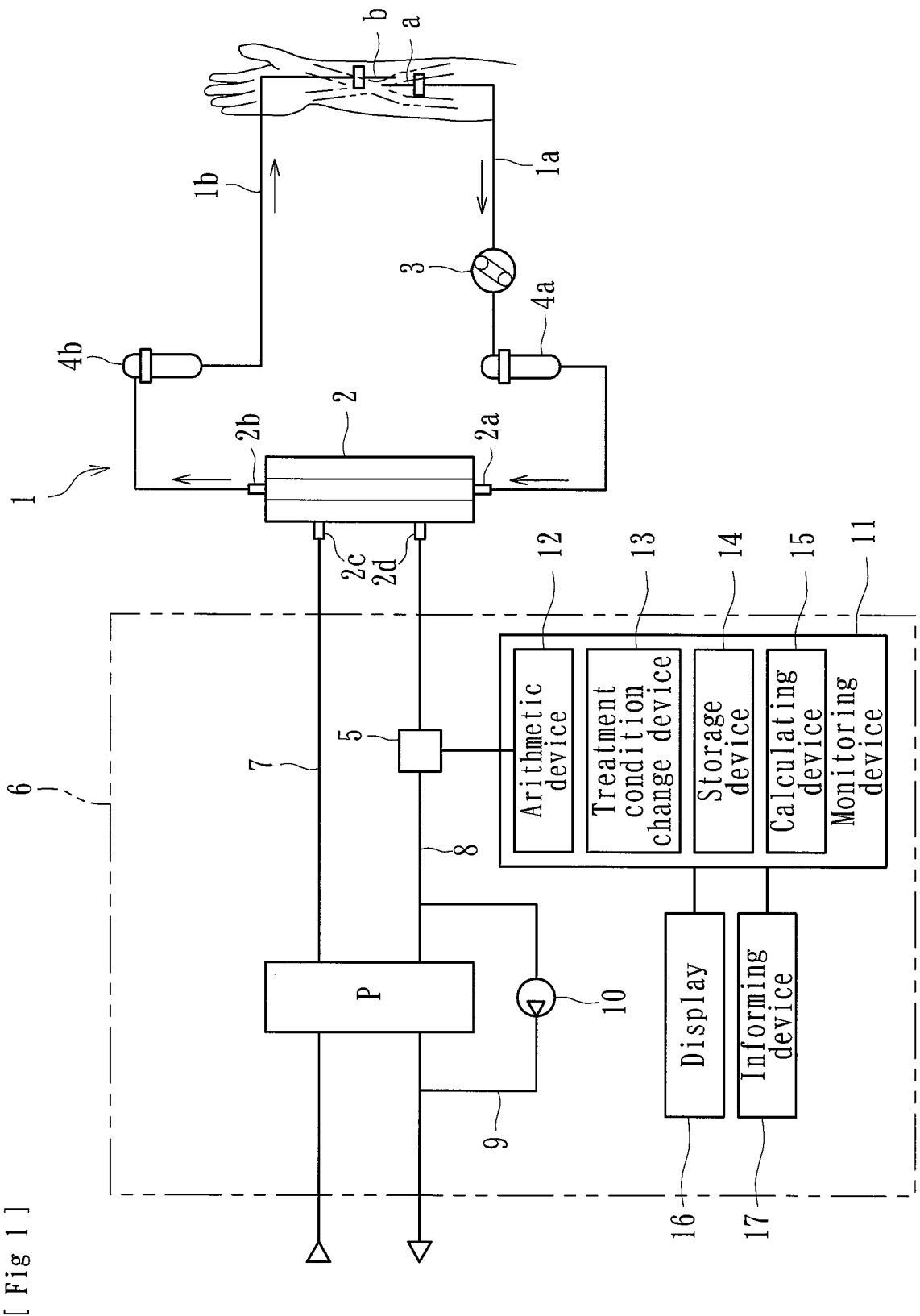
[Fig 1]

[Fig 2]
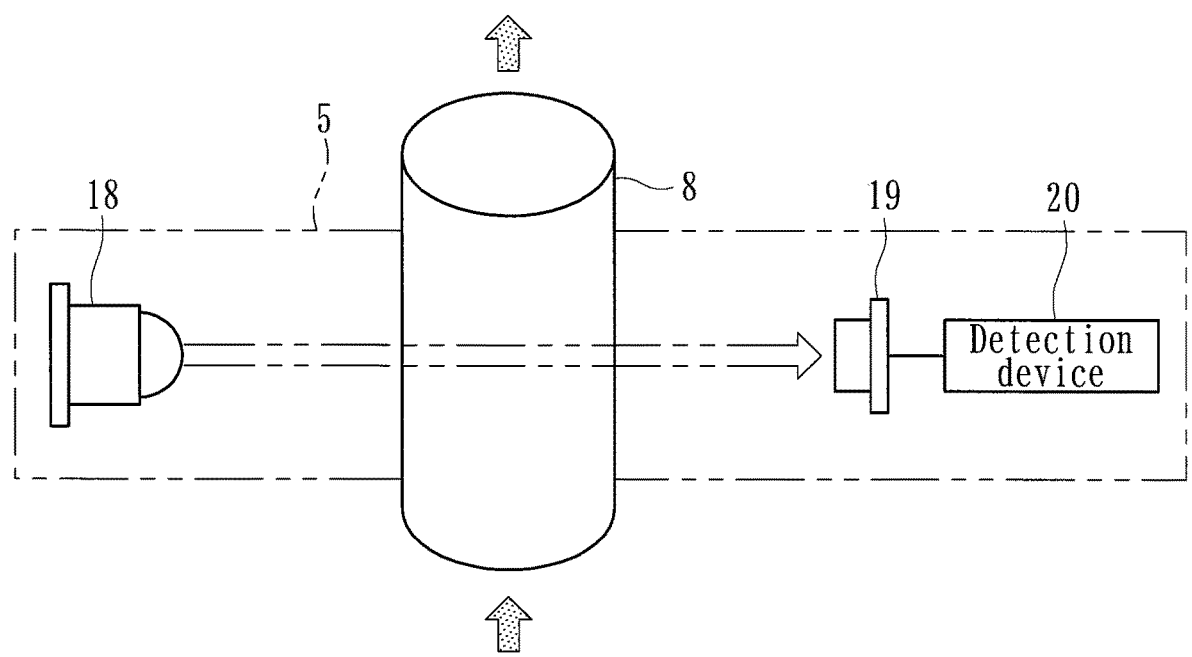

[Fig 3]
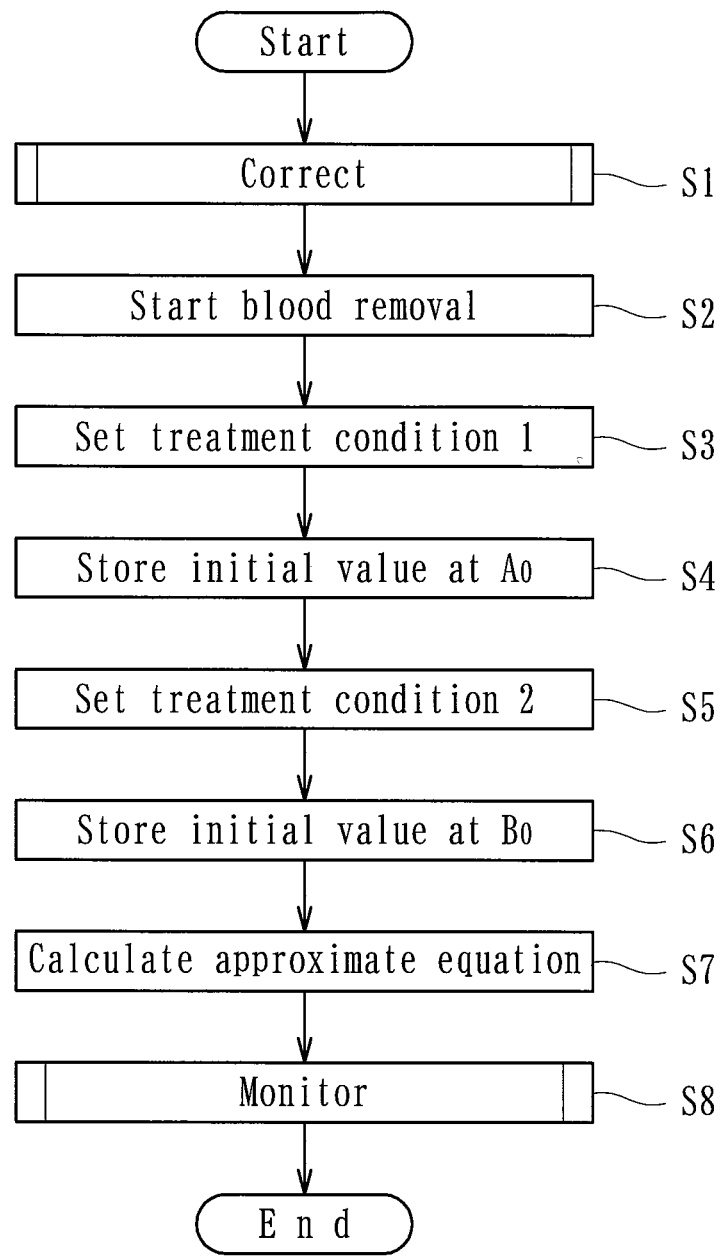

[Fig 4]
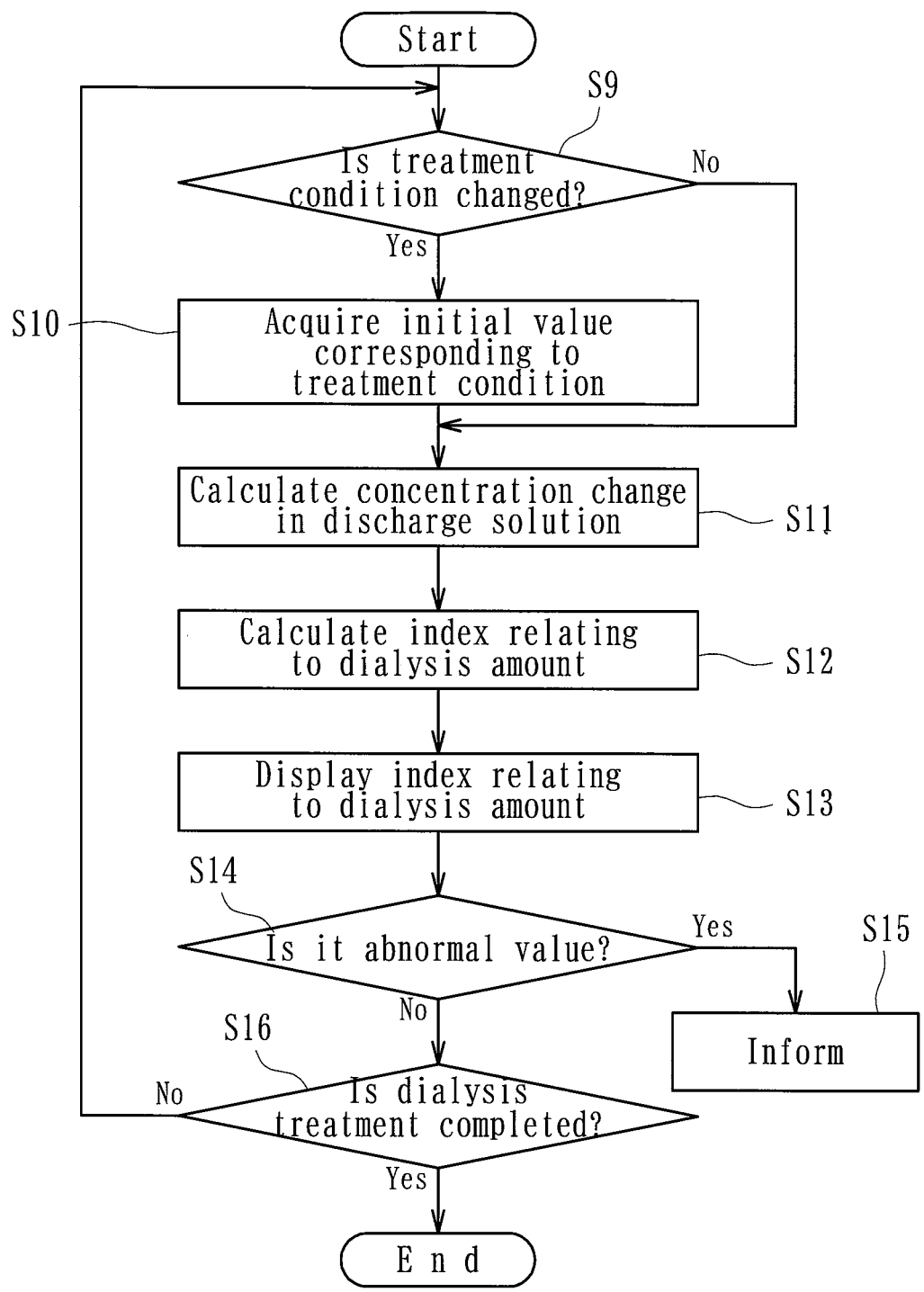

[Fig 5]
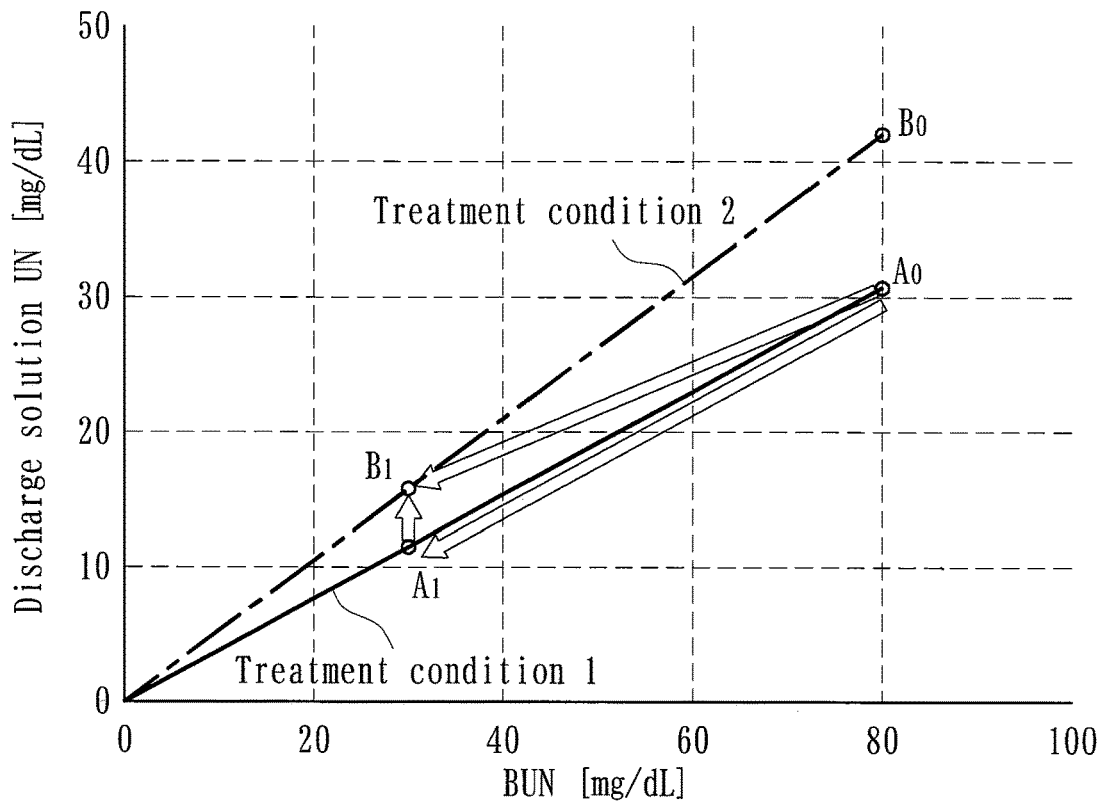
[Fig 6]
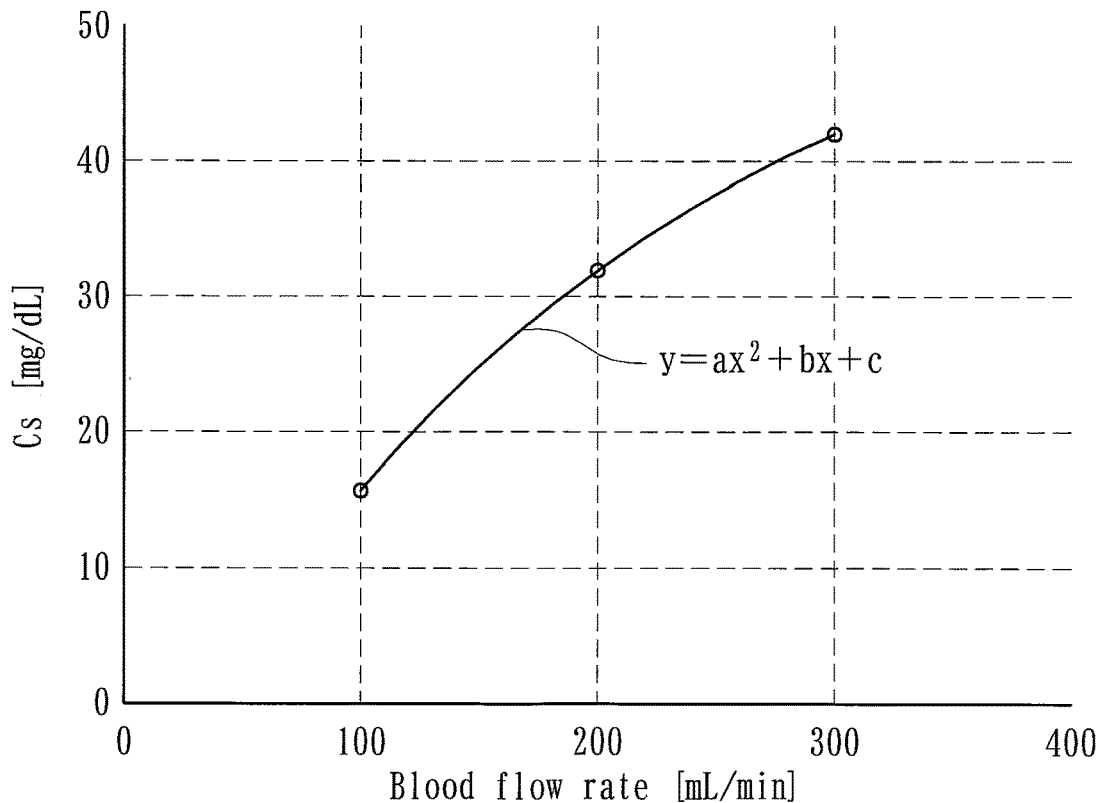

BLOOD PURIFICATION APPARATUS

CLAIM OF PRIORITY

This application is a continuation of International Application No. PCT/JP2014/072924, filed Sep. 1, 2014, which claims the benefit of the filing date of Japanese Patent Application No. 2013-181219, filed Sep. 2, 2013. The entirety of the contents of the above-referenced applications are incorporated by reference herein for all purposes.

FIELD

The present teachings relates to a blood purification apparatus which can perform real-time monitoring on a blood purification treatment state such as blood purification efficiency, based on a concentration change in a discharge solution.

BACKGROUND

Hemodialysis treatment is known as blood treatment for extracorporeally circulating the blood of a patient to purify the blood. According to the hemodialysis treatment, a dialyzer is provided as a blood purification device which can flow a dialysate. A blood circuit which extracorporeally circulates the blood of the patient is connected to the dialyzer, and the blood and the dialysate are brought into contact with each other via a semipermeable membrane of the dialyzer. In this manner, blood waste materials or excess water in the blood can be removed (removal of the excess water is called "ultrafiltration"). A configuration is adopted in which whereas the blood purified by the dialyzer returns into the body of the patient via a puncture needle, the blood waste materials or the excess water are discharged outward together with the dialysate via a dialysate discharge line.

Incidentally, the blood waste materials removed from the blood contain urea, uric acid, and creatinine. In particular, it is understood that a concentration change in the urea in the blood is an effective index which indicates a dialysis amount (dialysis efficiency). Accordingly, in order to obtain proper dialysis efficiency, monitoring the concentration change in the urea has been proposed. This concentration change in the urea can be usually monitored through a blood test which is regularly carried out. However, in that case, it is not possible to perform real-time monitoring on the concentration change in the urea during dialysis treatment.

Therefore, in the related art, a method has been alternatively proposed in which real-time detecting can be performed on the concentration change in the urea (index indicating "Kt/V") by providing a dialysate discharge line with a discharge solution concentration sensor which can detect concentration of a discharge solution (for example, refer to PTL 1 to PTL 4). The discharge solution concentration sensor in the related art includes a light emitting device (LED) which can emit light to the discharge solution from the dialyzer, a light receiving device which can receive the light transmitted through the discharge solution and transmitted from the LED, and a detection device which can detect light receiving intensity received by the light receiving device. The discharge solution concentration sensor is configured to be capable of detecting concentration of the discharge solution, based on the light receiving intensity detected by the detection device.

CITATION LIST

Patent Literature

PTL 1: Japanese Unexamined Patent Application Publication (Translation of PCT Application) No. 2002-516722;
PTL 2: Japanese Unexamined Patent Application Publication No. 2011-120821;
PTL 3: Japanese Unexamined Patent Application Publication No. 2011-120822; and
PTL 4: Japanese Unexamined Patent Application Publication No. 2011-120823, the teachings of which are all expressly incorporated by reference herein for all purposes.

SUMMARY

However, according to the above-described blood purification apparatus in the related art, for example, when treatment conditions such as a flow rate of the blood extracorporeally circulating in the blood circuit and a flow rate of the dialysate introduced into the blood purification device are changed during the treatment, concentration of a substance discharged from the blood to the discharge solution is inevitably changed, thereby causing a problem in that it becomes difficult to accurately detect the concentration. In particular, in some cases, the concentration change in the discharge solution is obtained, based on an initial value detected at earlier stage of the treatment and a measurement value when a predetermined period of time has elapsed, that is, when the concentration is detected by the discharge solution concentration sensor. Then, the real-time monitoring is performed on a blood purification treatment state such as a dialysis amount, based on the concentration change in the discharge solution. In these cases, when the treatment conditions are changed during the treatment, it is difficult to estimate the initial value under the changed treatment conditions. Consequently, there is a problem in that it is not possible to accurately monitor the blood purification treatment state.

The teachings herein are made in view of the above-described circumstances, and aims to provide a blood purification apparatus which can continue to accurately monitor a blood purification treatment state even if treatment conditions are changed during blood purification treatment.

According to the teachings herein, there is provided a blood purification apparatus including: a blood circuit for extracorporeally circulating the blood of a patient; a blood purification device that is connected to the blood circuit, and that purifies the extracorporeally circulating blood; a dialysate introduction line for introducing a dialysate into the blood purification device; a dialysate discharge line for discharging a discharge solution generated due to the blood purification performed by the blood purification device, from the blood purification device; a concentration detection device that can detect concentration of the discharge solution flowing in the dialysate discharge line; and an arithmetic device that can obtain a concentration change in the discharge solution, based on a first predetermined value detected by the concentration detection device and a second predetermined value detected after a predetermined period of time has elapsed therefrom. The blood purification apparatus can perform real-time monitoring on a blood purification treatment state, based on a concentration change in the discharge solution which is obtained by the arithmetic device. The blood purification apparatus further includes: a treatment condition change device that sets or changes treatment conditions as requested, and that causes the concentration detection device to previously detect the concentration of the discharge solution under the respective treatment conditions; and a storage device that stores the concentration of the discharge solution under the respective treatment conditions which is detected by the concentration detection device in the treatment condition change device, as the first predetermined value corresponding to the respective treatment conditions. When the treatment conditions are changed during blood purification treatment, the arithmetic device obtains the concentration change in the discharge solution, based on the first predetermined value corresponding to the changed treatment conditions among the first predetermined values stored in the storage device.

According to the teachings herein, the blood purification apparatus as is taught herein, the first predetermined value is an initial value when the blood purification treatment starts, and the second predetermined value is a current measurement value when the concentration detection device detects the concentration of the discharge solution.

According to the teachings herein, the blood purification apparatus according to the teachings herein further includes a calculating device for obtaining an approximate equation which approximates a relationship between the multiple treatment conditions stored in the storage device and the multiple first predetermined values corresponding to the respective treatment conditions. The first predetermined value corresponding to the treatment condition can be obtained, based on the approximate equation.

According to the teachings herein, the blood purification apparatus according to the teachings herein, the treatment conditions set or changed by the treatment condition change device include any factor or multiple factors selected from a flow rate of the blood extracorporeally circulating in the blood circuit, a flow rate of the dialysate introduced into the blood purification device, and velocity of ultrafiltration or substitution during the blood purification treatment.

According to the teachings herein, in the blood purification apparatus according the teachings herein, the concentration detection device includes: a light emitting device that can emit light to the discharge solution; a light receiving device that can receive the light which is transmitted through the discharge solution and which is transmitted from the light emitting device; and a detection device that can detect light receiving intensity received by the light receiving device. The concentration of the discharge solution can be detected, based on the light receiving intensity detected by the detection device, and the concentration detection device is corrected before the treatment condition change device sets or changes the treatment conditions as requested.

According to the teachings herein, a blood purification apparatus includes a treatment condition change device that sets or changes treatment conditions as requested, and that causes a concentration detection device to previously detect a concentration of a discharge solution under the respective treatment conditions, and a storage device that stores the concentration of the discharge solution under the respective treatment conditions which is detected by the concentration detection device in the treatment condition change device, as a first predetermined value corresponding to the respective treatment conditions. When the treatment conditions are changed during blood purification treatment, an arithmetic device obtains the concentration change in the discharge solution, based on the first predetermined value corresponding to the changed treatment conditions among the first predetermined values stored in the storage device. Therefore, the blood purification apparatus can continue to accurately monitor a blood purification treatment state even if the treatment conditions are changed during the blood purification treatment.

According to the teachings herein, the first predetermined value is an initial value when the blood purification treatment starts, and the second predetermined value is a current measurement value when the concentration detection device detects the concentration of the discharge solution. Accordingly, the blood purification apparatus can continue to obtain the concentration change between the initial value and the measurement value even if the treatment conditions are changed during the blood purification treatment. Therefore, the blood purification apparatus can accurately monitor a blood purification treatment state.

According to the teachings herein, the blood purification apparatus further includes a calculating device for obtaining an approximate equation which approximates a relationship between the multiple treatment conditions stored in the storage device and the multiple first predetermined values corresponding to the respective treatment conditions. The first predetermined value corresponding to the treatment condition can be obtained, based on the approximate equation. Therefore, even if the treatment conditions other than the treatment conditions changed by the treatment condition change device are changed during the blood purification treatment, the blood purification apparatus can obtain the first predetermined value corresponding to the treatment conditions, based on the approximate equation.

According to the teachings herein, the treatment conditions set or changed by the treatment condition change device include any factor or multiple factors selected from a flow rate of the blood extracorporeally circulating in the blood circuit, a flow rate of the dialysate introduced into the blood purification device, and velocity of ultrafiltration or substitution during the blood purification treatment. Therefore, the blood purification apparatus can correspond to a treatment condition change which is generally made.

According to the teachings herein, the concentration detection device includes a light emitting device that can emit light to the discharge solution, a light receiving device that can receive the light which is transmitted through the discharge solution and which is transmitted from the light emitting device, and a detection device that can detect light receiving intensity received by the light receiving device. The concentration of the discharge solution can be detected, based on the light receiving intensity detected by the detection device and the concentration detection device is corrected before the treatment condition change device sets or changes the treatment conditions as requested. Therefore, the blood purification apparatus can continue to accurately monitor a blood purification treatment state even if the treatment conditions are changed during the blood purification treatment.

BRIEF DESCRIPTION OF DRAWINGS

FIG. 1 is a schematic view illustrating a blood purification apparatus according to an embodiment of the present invention.

FIG. 2 is a schematic view illustrating a concentration detection device in the blood purification apparatus.

FIG. 3 is a flowchart illustrating control content of the blood purification apparatus.

FIG. 4 is a flowchart illustrating control content (monitoring content) of the blood purification apparatus.

FIG. 5 is a graph illustrating a relationship between discharge solutions UN and BUN corresponding to treatment conditions in the blood purification apparatus.

FIG. 6 is a graph illustrating an approximate equation obtained by a calculating device in the blood purification apparatus.

DETAILED DESCRIPTION

Hereinafter, an embodiment of the present invention will be described in detail with reference to the drawings.

A blood purification apparatus according to the present embodiment extracorporeally circulates the blood of a patient to purify the blood, and is applied to a hemodialysis apparatus used for hemodialysis treatment. As illustrated in FIG. 1, the hemodialysis apparatus is configured to mainly include a blood circuit 1 for extracorporeally circulating the blood of the patient, a dialyzer 2 functioning as a blood purification device, a discharge solution concentration sensor 5 functioning as a concentration detection device, a dialysis apparatus main body 6 which can perform ultrafiltration while supplying a dialysate to a dialyzer 2, a dialysate introduction line 7 and dialysate discharge line 8 which are arranged in the dialysis apparatus main body 6, a monitoring device 11, a display 16, and an informing device 17.

As illustrated in the drawing, the blood circuit 1 is configured to mainly include an arterial blood circuit 1a and a venous blood circuit 1b which are formed of a flexible tube. The dialyzer 2 is connected between the arterial blood circuit 1a and the venous blood circuit 1b. An arterial puncture needle (a) is connected to a distal end of the arterial blood circuit 1a. A peristaltic blood pump 3 and an air trap chamber 4a for bubble removal are arranged in an intermediate section of the arterial blood circuit 1a. Meanwhile, a venous puncture needle (b) is connected to a distal end of the venous blood circuit 1b. An air trap chamber 4b for bubble removal is connected to an intermediate portion of the venous blood circuit 1b.

Then, if the blood pump 3 is rotated in a state where the arterial puncture needle (a) and the venous puncture needle (b) puncture a patient, the blood of the patient is subjected to bubble removal in the air trap chamber 4a, and passes through the arterial blood circuit 1a. The blood of the patient reaches the dialyzer 2, and is subjected to blood purification and ultrafiltration by the dialyzer 2. Thereafter, the blood of the patient returns into the body of the patient after passing through the venous blood circuit 1b while being subjected to the bubble removal in the air trap chamber 4b. In this manner, the blood of the patient is purified by the dialyzer 2 during a process while the blood of the patient is extracorporeally circulated in the blood circuit 1.

In the dialyzer 2 (blood purification device), a housing unit thereof has a blood introduction port 2a, a blood extraction port 2b, a dialysate introduction port 2c, and a dialysate extraction port 2d. Among these, a proximal end of the arterial blood circuit 1a is connected to the blood introduction port 2a, and a proximal end of the venous blood circuit 1b is connected to the blood extraction port 2b, respectively. In addition, the dialysate introduction port 2c and the dialysate extraction port 2d are respectively connected to each distal end of the dialysate introduction line 7 and the dialysate discharge line 8 which extend from the dialysis apparatus main body 6.

Multiple hollow fibers are accommodated inside the dialyzer 2. The inside of the hollow fiber functions as a blood flow route. A section between an outer peripheral surface of the hollow fiber and an inner peripheral surface of the housing unit functions as a dialysate flow route. Many minute holes (pores) penetrating the inner peripheral surface and the outer peripheral surface are formed in the hollow fiber, thereby forming a hollow fiber membrane. The dialyzer 2 is configured so that blood waste materials or excess water in the blood can permeate the dialysate through the membrane.

The dialysis apparatus main body 6 is configured to have a duplex pump P, a bypass line 9 which is connected to the dialysate discharge line 8 while bypassing a pump chamber on a side where the duplex pump P discharges a solution in the dialysate discharge line 8, and an ultrafiltration pump 10 which is connected to the bypass line 9. The duplex pump P is arranged across the dialysate introduction line 7 and the dialysate discharge line 8. The dialysate is introduced into the dialyzer 2 from the dialysate introduction line 7, and the dialysate introduced into the dialyzer 2 is discharged from the dialysate discharge line 8 together with the blood waste materials in the blood.

One end of the dialysate introduction line 7 is connected to the dialyzer 2 (dialysate introduction port 2c), and the other end is connected to a dialysate supply apparatus (not illustrated) which produces the dialysate having predetermined concentration. One end of the dialysate discharge line 8 is connected to the dialyzer 2 (dialysate extraction port 2d), and the other end is connected to a solution discharge device (not illustrated). A configuration is adopted in which the dialysate introduction line 7 introduces the dialysate supplied from the dialysate supply apparatus into the dialyzer 2, and the dialysate discharge line 8 discharges a discharge solution generated from the blood purified by the dialyzer 2, from the dialyzer 2 toward the solution discharge device.

The ultrafiltration pump 10 removes water (excess water) from the blood of the patient which flows in the dialyzer 2. That is, if the ultrafiltration pump 10 is rotated, a volume of a liquid discharged from the dialysate discharge line 8 is larger than the amount of the dialysis introduced from the dialysate introduction line 7. Thus, the water is removed from the blood by the amount of the increased volume. The water may be removed from the blood of the patient by using other devices (for example, those which use a so-called balancing chamber) in addition to the ultrafiltration pump 10.

The discharge solution concentration sensor 5 (concentration detection device) is arranged in the dialysate discharge line 8 inside the dialysis apparatus main body 6, and can detect concentration (for example, concentration of a substance such as urea and uric acid which are contained in a discharge solution) of a liquid (in the present embodiment, a discharge solution discharged from the dialyzer 2 functioning as the blood purification device) which is caused to flow due to the blood purification. As illustrated in FIG. 2, the discharge solution concentration sensor 5 is configured to mainly include a light emitting device 18, a light receiving device 19, and a detection device 20. The light emitting device 18 and the light receiving device 19 are respectively arranged at positions which face each other by interposing the dialysate discharge line 8 therebetween.

The light emitting device 18 is a light source having an LED which can emit light to a liquid (in the present embodiment, the discharge solution discharged from the dialyzer 2), and the light transmitted through the liquid can be received by the light receiving device 19. The light receiving device 19 according to the present embodiment has a light receiving element which can generate a voltage corresponding to intensity of the received light. The detection device 20 is configured to be capable of detecting concentration of the discharge solution, based on the voltage corresponding to the light receiving intensity.

In this manner, if the light is emitted from the light emitting device 18 in a state where the discharge solution flows in the dialysate discharge line 8, the emitted light is transmitted through the discharge solution flowing in the dialysate discharge line 8. Accordingly, the light is absorbed in response to the concentration of the discharge solution, and thereafter the light is received by the light receiving device 19. Then, a signal of the light receiving intensity (that is, a voltage generated in response to the light receiving intensity) received by the light receiving device 19 is transmitted to the detection device 20. The concentration of the discharge solution flowing in the dialysate discharge line 8 is detected by the detection device 20.

The discharge solution concentration sensor 5 according to the present embodiment employs an optical sensor which emits ultraviolet rays having a wavelength of approximately 300 nm (280 nm to 320 nm) from the light emitting device 18. However, an optical sensor which emits another light such as infrared rays may be employed. Alternatively, a sensor of a different type from that of the optical sensor, such as an enzyme sensor, may be employed. In addition, the discharge solution concentration sensor 5 according to the present embodiment is arranged on the further upstream side (side connected to the dialyzer 2) from the duplex pump P in the dialysate discharge line 8, but may be arranged on the further downstream side from the duplex pump P.

The monitoring device 11 is arranged in the dialysis apparatus main body 6, and includes microcomputer which is electrically connected to the discharge solution concentration sensor 5. The monitoring device 11 is configured to mainly include an arithmetic device 12, a treatment condition change device 13, a storage device 14, and a calculating device 15. According to the present embodiment, the monitoring device 11, the display 16, and the informing device 17 are electrically connected to each other, and can perform real-time displaying and informing based on monitoring.

Based on a first predetermined value detected by the discharge solution concentration sensor 5 and a second predetermined value detected after a predetermined period of time has elapsed therefrom, the arithmetic device 12 can obtain a concentration change (for example, a ratio or a difference between the first predetermined value and the second predetermined value) in the discharge solution. The monitoring device 11 is configured so that real-time monitoring can be performed on a blood purification treatment state, based on the obtained concentration change in the discharge solution. According to the present embodiment, the first predetermined value is an initial value when the blood purification treatment starts (initial stage of treatment after blood removal), and the second predetermined value is a current measurement value when the discharge solution concentration sensor 5 detects the concentration of the discharge solution (monitoring target time for monitoring the blood purification treatment state).

For example, if based on the concentration change in the discharge solution which is obtained by the arithmetic device 12, an index relating to a dialysis amount (dialysis efficiency) such as a standard dialysis amount (Kt/V) and a urea removal rate (URR) is obtained, the real-time monitoring can be performed on a blood purification state during the blood purification treatment. Here, the standard dialysis amount (Kt/V) is an index which can be obtained through calculation by substituting a predetermined arithmetic expression for a concentration change in urea nitrogen contained in the discharge solution when the hemodialysis treatment starts and at the current time (monitoring time), an ultrafiltration amount during the hemodialysis treatment (blood purification treatment), and a treatment period of time for hemodialysis treatment. The urea removal rate (URR) is an index which can be obtained through calculation by substituting a predetermined arithmetic expression for the concentration change in urea nitrogen contained in the discharge solution when the hemodialysis treatment starts and at the current time (monitoring time). For example, the standard dialysis amount (Kt/V) and the urea removal rate (URR) can be obtained by the following arithmetic expressions.

Standard dialysis amount $(Kt/V) = -\ln(C(e)/C(s) - 0.008\,t) + (4 - 3.5 \times C(e)/C(s)) \times (VUF/DW)$ (Arithmetic Expression 1)

Urea removal rate $(URR) = (1 - (C(e)/C(s))) \times 100$ (Arithmetic Expression 2)

wherein, C(s) represents urea nitrogen concentration (initial value) when hemodialysis treatment starts, C(e) represents urea nitrogen concentration at the current time (at the monitoring time), VUF represents an ultrafiltration amount, and DW represents a patient's dry weight. With regard to Kt/V obtained by Arithmetic Expression 1 above, K represents a clearance, t represents an elapsed period of time for dialysis treatment, and V represents a urea distribution volume.

The treatment condition change device 13 sets or changes treatment conditions as requested when blood purification treatment starts (in the present embodiment, an initial stage of the blood purification treatment after blood removal), and causes the discharge solution concentration sensor 5 to previously detect the concentration of the discharge solution under the respective conditions. The treatment conditions set or changed by the treatment condition change device 13 according to the present embodiment include any factor or multiple factors selected from a flow rate of the blood extracorporeally circulating in the blood circuit 1 (for example, rotating speed of the blood pump 3), a flow rate of the dialysate introduced into the dialyzer 2 (for example, rotating speed of the duplex pump P), and velocity of ultrafiltration or substitution (for example, rotating speed of the ultrafiltration pump 10 or a substitution pump (not illustrated)) during the blood purification treatment. However, the other treatment conditions which are supposed to be changed during the treatment may be selected.

The storage device 14 causes the treatment condition change device 13 to store concentration of the discharge solution under the respective treatment conditions which is detected by the discharge solution concentration sensor 5, as the first predetermined value corresponding to each treatment condition (in the present embodiment, the urea nitrogen concentration C(s) serving as an initial value under each condition). Even if the treatment condition is changed during the process of the blood purification treatment, the storage device 14 can refer the initial value (C(s)) of the concentration of the discharge solution under the changed treatment condition, to the monitoring device 11.

Here, the arithmetic device 12 is configured to obtain a concentration change in the discharge solution, based on the first predetermined value (initial value) corresponding to the changed treatment condition among the first predetermined values (initial values) stored in the storage device 14 during the blood purification treatment (after the treatment condition change device 13 sets or changes the treatment condition, and after the storage device 14 stores the concentration of the discharge solution under each treatment condition).

For example, as illustrated in a relationship between urea nitrogen concentration in the blood (BUN) and urea nitrogen concentration in the discharge solution (discharge solution UN) in FIG. 5, when Treatment Condition 1 is changed to Treatment Condition 2 after the blood purification treatment (hemodialysis treatment) is performed under Treatment Condition 1 from an initial time point A0 until a time point A1, the discharge solution concentration sensor 5 can detect the concentration (discharge solution UN) of the discharge solution under Treatment Condition 2 at a time point B1. Normally, the concentration (discharge solution UN) of the discharge solution at an initial time point B0 cannot be retroactively detected.

If a concentration change in the discharge solution is obtained based on the concentration of the discharge solution at the initial time point A0 under Treatment Condition 1 and the concentration of the discharge solution at the time point B1 under Treatment Condition 2, an error occurs as is understood from FIG. 5. Therefore, in this case, if the treatment condition is changed during the process of the blood purification treatment, it becomes difficult to obtain the concentration change in the discharge solution. Consequently, it is no longer possible to continuously monitor a blood purification treatment state (dialysis amount or the like) to be recognized based on the concentration change in the discharge solution.

In contrast, according to the present embodiment, the treatment condition change device 13 previously sets or changes the treatment conditions which are supposed to be changed during the treatment, the discharge solution concentration sensor 5 detects the concentration (urea nitrogen concentration) of the discharge solution under the respective treatment conditions (for example, Treatment Conditions 1 and 2), and the storage device 14 stores the concentration as the initial value C(s) at the initial time points A0 and B0 under the respective treatment conditions. Accordingly, even if the treatment condition is changed from Treatment Condition 1 to Treatment condition 2 during the process of the blood purification treatment, it is possible to refer to the initial value C(s) under Treatment Condition 2 after the treatment condition is changed. Therefore, even if the treatment condition is changed during the process of the blood purification treatment, it is possible to easily and accurately obtain the concentration change in the discharge solution, and it is possible to continuously monitor the blood purification treatment state (dialysis amount or the like).

The calculating device 15 obtains an approximation equation approximate to a relation between the multiple treatment conditions and the multiple first predetermined values (initial values) corresponding to the respective treatment conditions which are stored in the storage device 14, and can obtain the first predetermined value (initial value) corresponding to the treatment condition, based on the obtained approximate equation. For example, a configuration is adopted in which the treatment condition change device 13 sets or change the rotating speed of the blood pump 3 as requested, in which as illustrated in FIG. 6, under multiple (three in the present embodiment) treatment conditions (conditions except for the blood flow rate are the same) by setting a flow rate of the blood extracorporeally circulating in the blood circuit (blood flow rate) to 100 (mL/min), 200 (mL/min), and 300 (mL/min), the storage device 14 stores the concentration (urea nitrogen concentration) of the discharge solution which is detected by the discharge solution concentration sensor 5 under the respective treatment conditions, as the respective initial values (C(s)), and in which the calculating device 15 obtains an approximation equation (for example, quadratic equation of $y=ax^2+bx+c$) for the blood flow rate of the multiple initial values (C(s)).

In this manner, without being limited to the treatment condition set or changed by the treatment condition change device 13, based on the approximate equation obtained by the calculating device 15, it is possible to obtain the initial value C(s) of the concentration (urea nitrogen concentration) of the discharge solution under the changed treatment condition. According to the present embodiment, the treatment condition change device 13 changes the blood flow rate, thereby changing the treatment condition. However, the other treatment conditions (as previously described, the flow rate of the dialysate to be introduced into the dialyzer 2, the velocity of the ultrafiltration or substitution during the blood purification treatment, and the like) may be changed so that the calculating device 15 obtains the approximate equation under the respective treatment conditions.

The display 16 includes a touch panel disposed in the dialysis apparatus main body 6, and can display various information items (a treatment state of a patient or a setting state of an apparatus) on the screen during treatment. In addition, the informing device 17 can inform a standby health care worker of abnormality when any abnormalities are caused in the patient or the apparatus during the treatment. For example, the informing device 17 is configured to include a speaker or a warning light which can output a warning. When the patient or the apparatus is abnormal, the display 16 may display the abnormality.

Next, control content of the monitoring device 11 in the blood purification apparatus according to the present embodiment will be described with reference to a flowchart in FIG. 3.

First, after the discharge solution concentration sensor 5 is corrected in a predetermined manner in S1, the blood pump 3 is rotated so as to start blood removal (S2). In this manner, the blood is extracorporeally circulated in the blood circuit 1 from the arterial puncture needle (a) toward the venous puncture needle (b). At this time, the blood is set to be extracorporeally circulated under a predetermined condition. However, the blood purification treatment (dialysis treatment) may be performed, or the blood purification treatment may not be performed.

Then, the treatment condition change device 13 set the treatment condition to Treatment Condition 1 while the blood is extracorporeally circulated (S3). The discharge solution concentration sensor 5 detects the concentration (urea nitrogen concentration) of the discharge solution under Treatment Condition 1, and the storage device 14 stores the detected concentration of the discharge solution as the initial value C(s) (first predetermined value) at the initial time point A0 (S4). Furthermore, the treatment condition change device 13 changes the treatment condition to Treatment Condition 2 while the blood is continuously extracorporeally circulated (S5). The discharge solution concentration sensor 5 detects the concentration (urea nitrogen concentration) of the discharge solution under Treatment Condition 2, and the storage device 14 stores the detected concentration of the discharge solution as the initial value C(s) (first predetermined value) at the initial time point B0 (S6). In the flowchart, the treatment condition is changed from Treatment Condition 1 to only Treatment Condition 2. However, it is preferable that the treatment condition is continuously changed to other multiple treatment conditions so as to store the initial value C(s) (first predetermined value).

Thereafter, the process proceeds to S7, and the calculating device 15 obtains the approximate equation, based on the initial value C(s) under each treatment condition stored in the storage device 14. Preparation (process of acquiring the initial value under each treatment condition) is completed, and the blood purification treatment which is a monitoring target starts (S8). The monitoring in the blood purification treatment will be described below with reference to a flowchart in FIG. 4.

First, in S9, it is determined whether or not the treatment condition is changed. When the treatment condition is changed, the process proceeds to S10. The initial value C(s) corresponding to the changed treatment condition is obtained from the information items stored in the storage device 14 or the approximate equation calculated by the calculating device 15, and the process proceeds to S11. When it is determined in S9 that the treatment condition is not changed, S10 is skipped, and the process proceeds to S11. In S11, the discharge solution concentration sensor 5 detects the concentration of the discharge solution flowing in the dialysate discharge line 8, and the arithmetic device 12 obtains the concentration change in the discharge solution.

Thereafter, the index relating to the dialysis amount (for example, the above-described standard dialysis amount (Kt/V) or urea removal rate (URR)), based on the concentration change in the discharge solution obtained by the arithmetic device 12, is calculated (S12). The display 16 displays the index relating to the calculated dialysis amount (S13). Instead of or together with the standard dialysis amount (Kt/V) or urea removal rate (URR), other indexes relating to the dialysis amount may be calculated or displayed.

Then, it is determined whether or not the index relating to the dialysis amount which is obtained in S12 is an abnormal value (S14). When it is determined as the abnormal value, the process proceeds to S15, and the informing device 17 informs a user of the abnormality (the display 16 may display the abnormality). In contrast, when it is determined that the index relating to the dialysis amount is not the abnormal value, the process proceeds to S16, and it is determined whether or not the dialysis treatment is completed. When it is determined in S16 that the dialysis treatment is completed, a series of control is completed. When it is determined in S16 that the dialysis treatment is not completed, the process returns to S9. It is determined whether or not the treatment condition is changed again, and a series of control is repeatedly performed.

According to the above-described embodiment, the blood purification apparatus includes the treatment condition change device 13 that sets or changes the treatment condition as requested, and that causes the discharge solution concentration sensor 5 to previously detect the concentration of the discharge solution under each treatment condition, and the storage device 14 that stores the concentration of the discharge solution under each treatment condition which is detected by the discharge solution concentration sensor 5 in the treatment condition change device 13, as the first predetermined value (initial value C(s) in the present embodiment) corresponding to each treatment condition. When the treatment condition is changed during the blood purification treatment, the arithmetic device 12 obtains the concentration of the discharge solution, based on the first predetermined value corresponding to the changed treatment condition among the first predetermined values stored in the storage device 14. Accordingly, even when the treatment condition is changed during the blood purification treatment, it is possible to continuously and accurately monitor a blood purification treatment state.

In addition, the first predetermined value according to the present embodiment is set to function as the initial value when the blood purification treatment starts (initial stage of the blood purification treatment after blood removal starts). The second predetermined value is set to function as the current measurement value obtained when the discharge solution concentration sensor 5 detects the concentration of the discharge solution. Accordingly, even when the treatment condition is changed during the blood purification treatment, it is possible to continuously obtain a concentration change between the initial value and the measurement value. Therefore, it is possible to accurately monitor a blood purification treatment state.

Furthermore, according to the present embodiment, the blood purification apparatus includes the calculating device 15 which can obtain the approximation equation which approximates to a relationship between the multiple treatment conditions stored in the storage device 14 and the multiple first predetermined values (initial values C(s)) corresponding to each treatment condition. Based on the approximate equation, the first predetermined value corresponding to the treatment condition can be obtained. Accordingly, during the blood purification treatment, even when the treatment condition is changed to any other treatment condition except for the treatment condition changed by the treatment condition change device 13, it is possible to continuously obtain the first predetermined value corresponding to the treatment conditions, based on the approximate equation.

Moreover, according to the present embodiment, the treatment conditions set or changed by the treatment condition change device 13 include any factor or multiple factors selected from a flow rate of the blood extracorporeally circulating in the blood circuit 1, a flow rate of the dialysate introduced into the dialyzer 2, and velocity of ultrafiltration or substitution during the blood purification treatment. Therefore, the blood purification apparatus can correspond to a treatment condition change which is generally made (that is, treatment condition which is supposed to be changed).

In addition, the discharge solution concentration sensor 5 includes the light emitting device 18 that can emit light to the discharge solution, the light receiving device 19 that can receive the light which is transmitted through the discharge solution and which is transmitted from the light emitting device 18, and the detection device 20 that can detect light receiving intensity received by the light receiving device 19. Based on the light receiving intensity detected by the detection device 20, the concentration of the discharge solution can be obtained, and the discharge solution concentration sensor 5 is corrected before the treatment condition change device 13 sets or changes the treatment condition as requested. Accordingly, even when the treatment condition is changed during the blood purification treatment, it is possible to continuously and more accurately monitor a blood purification treatment state.

Hitherto, the present embodiment has been described. However, the present invention is not limited thereto. For example, the index relating to the dialysis amount serving as a monitoring target is not limited to the standard dialysis amount (Kt/V) or the urea removal rate (URR). Other indexes may be obtained so as to perform real-time monitoring during the blood purification treatment. In addition, the calculating device 15 may not be provided, and many treatment conditions which are supposed to be changed may be set so as to previously obtain the first predetermined value corresponding to each treatment value. In this manner, even when treatment conditions are changed during the treatment, the blood purification apparatus may correspond to a treatment condition change. According to the present embodiment, the present invention is applied to a hemodialysis apparatus. However, the present invention may be applied to a blood purification apparatus used for other treatments (hemofiltration or hemodiafiltration) in which blood purification is performed while the blood is extracorporeally circulated.

A blood purification apparatus includes a treatment condition change device that sets or changes treatment conditions as requested, and that causes a concentration detection device to previously detect concentration of a discharge solution under each treatment condition, and a storage device that stores the concentration of the discharge solution under each treatment condition which is detected by the concentration detection device in the treatment condition change device, as a first predetermined value corresponding to each treatment condition. When the treatment condition is changed during blood purification treatment, the concentration of the discharge solution is obtained, based on the first predetermined value corresponding to the changed treatment condition among the first predetermined values stored in the storage device. In this case, the blood purification apparatus can be applied to those which have other additional functions.

REFERENCE SIGNS LIST

1 BLOOD CIRCUIT
1a ARTERIAL BLOOD CIRCUIT
1b VENOUS BLOOD CIRCUIT
2 DIALYZER (BLOOD PURIFICATION DEVICE)
3 BLOOD PUMP
4a, 4b AIR TRAP CHAMBER
5 DISCHARGE SOLUTION CONCENTRATION SENSOR (CONCENTRATION DETECTION DEVICE)
6 DIALYSIS APPARATUS MAIN BODY
7 DIALYSATE INTRODUCTION LINE
8 DIALYSATE DISCHARGE LINE
9 BYPASS LINE
10 ULTRAFILTRATION PUMP
11 MONITORING DEVICE
12 ARITHMETIC DEVICE
13 TREATMENT CONDITION CHANGE DEVICE
14 STORAGE DEVICE
15 CALCULATING DEVICE
16 DISPLAY
17 INFORMING DEVICE
18 LIGHT EMITTING DEVICE
19 LIGHT RECEIVING DEVICE
20 DETECTION DEVICE

We claim:

1. A blood purification apparatus comprising:
a blood circuit for extracorporeally circulating blood of a patient;
a blood purification device that is connected to the blood circuit, and that purifies the extracorporeally circulating blood;
a dialysate introduction line for introducing a dialysate into the blood purification device;
a dialysate discharge line for discharging a discharge solution generated from the blood purification device due to blood purification performed by the blood purification device;
a concentration detection device that detects a concentration of the discharge solution flowing in the dialysate discharge line;
an arithmetic device that obtains a change in the concentration of the discharge solution; and
a treatment condition change device that sets or changes treatment conditions as requested;
wherein the blood purification apparatus is configured to perform real-time monitoring on a blood purification treatment state, based on a concentration change in the discharge solution which is obtained by the arithmetic device, and the blood purification apparatus further comprises:
a storage device that stores initial values that are correlated with multiple treatment conditions and stored as multiple first predetermined values, wherein the concentration of the discharge solution is detected under each of the multiple treatment conditions by the concentration detection device;
wherein, when the treatment conditions are changed during blood purification treatment by the treatment condition change device, the arithmetic device obtains the concentration change in the discharge solution based on a second predetermined value which is a current measurement value detected under the changed treatment condition and one of the multiple first predetermined values corresponding to the changed treatment conditions among the multiple first predetermined values stored in the storage device so that the blood purification treatment state is monitored in real time;
wherein the blood purification apparatus executes a determination process that determines whether or not the treatment conditions are changed, which is repeated until the blood purification treatment is ended;
wherein when the determination process determines that the treatment conditions are changed, a first predetermined value, from the multiple first predetermined values, that corresponds to the changed treatment condition is obtained from the storage device that stores each of the multiple first predetermined values corresponding to multiple treatment conditions, and the concentration change in the discharge solution is obtained based on a difference between the first predetermined value from the storage device and the second predetermined value to be detected; and
wherein when the determination process determines that the treatment condition is not changed, the concentration change in the discharge solution is obtained based upon the first predetermined value, from the multiple predetermined values, corresponding to the current treatment condition from the storage device and the second predetermined value to be detected.

2. The blood purification apparatus according to claim 1, further comprising:
a calculating device for obtaining an approximate equation which approximates a relationship between multiple treatment conditions stored in the storage device and the multiple first predetermined values corresponding to the multiple treatment conditions,
a monitoring device;
wherein the multiple first predetermined values corresponding to the treatment conditions are obtainable, based on the approximate equation; and
wherein the monitoring device comprises a calculating device.

3. The blood purification apparatus according to claim 1, wherein the concentration detection device further includes:
a detection device that detects light receiving intensity received by the light receiver,
wherein the concentration of the discharge solution is detected, based on the light receiving intensity detected by the detection device, and the concentration detection device is corrected before the treatment condition change device sets or changes the treatment conditions as requested.

4. The blood purification apparatus according to claim 2, wherein the concentration detection device further includes:
   a detection device that detects light receiving intensity received by the light receiver,
   wherein the concentration of the discharge solution is detected, based on the light receiving intensity detected by the detection device, and the concentration detection device is corrected before the treatment condition change device sets or changes the treatment conditions as requested.

5. The blood purification apparatus according to claim 1, wherein the concentration detection device further includes:
   a light transmitter and a light receiver;
   a detection device that detects light receiving intensity received by the light receiver,
   wherein the concentration of the discharge solution is detected, based on the light receiving intensity detected by the detection device, and the concentration detection device is corrected before the treatment condition change device sets or changes the treatment conditions as requested; and
   wherein the light transmitter and the light receiver oppose one another by interposing the dialysate discharge line therebetween so that an intensity of light is transmitted through the dialysate discharge line.

6. The blood purification apparatus according to claim 1, wherein the concentration change in the discharge solution provides an index that relates the concentration change in the discharge solution to a dialysis amount (Kt/V).

7. The blood purification apparatus according to claim 6, wherein the concentration detection device further includes:
   a light transmitter and a light receiver;
   a detection device that detects light receiving intensity received by the light receiver,
   wherein the concentration of the discharge solution is detected, based on the light receiving intensity detected by the detection device, and the concentration detection device is corrected before the treatment condition change device sets or changes the treatment conditions as requested.

8. The blood purification apparatus according to claim 1, wherein the concentration change in the discharge solution provides an index that relates the concentration change in the discharge solution to a urea removal rate (URR).

9. The blood purification apparatus according to claim 6, including a display device that displays the index relating to the dialysis amount, and an informing device which informs an individual of an abnormal value.

10. The blood purification apparatus according to claim 1, wherein the concentration detection device is a discharge solution concentration sensor that employs an enzyme sensor, and the concentration detection device is arranged on an upstream side from a duplex pump in the dialysate discharge line.

11. The blood purification apparatus according to claim 7, wherein the light transmitter is a light emitting diode (LED).

12. The blood purification apparatus according to claim 7, wherein the light receiver includes a light receiving element that generates a voltage corresponding to an intensity of light received by the light receiver.

13. The blood purification apparatus according to claim 6, including a display device that displays the index.

14. The blood purification apparatus according to claim 13, including an informing device which informs an individual of an abnormal value, and the informing device includes a speaker or a warning light that outputs a warning indicating the abnormal value.

15. The blood purification apparatus according to claim 1, wherein the arithmetic device corrects the concentration of the discharge solution before the treatment condition change device sets or changes the treatment condition.

16. The blood purification apparatus according to claim 1, wherein the treatment conditions are flow rate of the blood extracorporeally circulating in the blood circuit, flow rate of the dialysate introduced into a dialyzer, and velocity of ultrafiltration or substitution during the blood purification treatment.

17. A method comprising:
   extracorporeally circulating blood of a patient through a blood circuit;
   purifying the blood that is extracorporeally circulating with a blood purification device that is connected to the blood circuit;
   introducing a dialysate into the blood purification device through a dialysate introduction;
   discharging a discharge solution generated from the blood purification device due to blood purification performed by the blood purification device through a dialysate discharge line;
   detecting a concentration of the discharge solution flowing in the dialysate discharge line with a concentration detection device;
   obtaining a change in the concentration of the discharge solution via an arithmetic device; and
   changing treatment conditions as requested by a treatment condition change device that sets or changes the treatment conditions;
   performing real-time monitoring of a blood purification treatment state, based on a concentration change in the discharge solution which is obtained by the arithmetic device;
   storing initial values, in a storage device, that that are correlated with multiple treatment conditions and stored as multiple first predetermined values, wherein the concentration of the discharge solution is detected under each of the multiple treatment conditions by the concentration detection device;
   wherein, when the treatment conditions are changed during blood purification treatment by the treatment condition change device, the arithmetic device obtains the concentration change in the discharge solution based on a second predetermined value which is a current measurement value detected under the changed treatment condition and one of the multiple first predetermined values corresponding to the changed treatment conditions among the multiple first predetermined values stored in the storage device so that the blood purification treatment state is monitored in real time;
   executing a determination process that determines whether or not the treatment conditions are changed, and repeating the determination process until the blood purification treatment is ended;
   determining that the treatment conditions are changed from a first predetermined value, based on a difference between the first predetermined value from the storage device and the second predetermined value to be detected; and
   determining that the treatment condition is not changed, by the concentration change in the discharge solution from the first predetermined value corresponds to the second predetermined value to be detected.

18. The method according to claim 17, further comprising:
- obtaining an approximate equation which approximates a relationship between multiple treatment conditions stored in the storage device and the multiple first predetermined values corresponding to the multiple treatment conditions with a calculating device,
- a monitoring device;
- wherein the multiple first predetermined values corresponding to the treatment conditions are obtainable, based on the approximate equation.

19. The method according to claim 17, wherein the concentration detection device further includes:
- a detection device that detects light receiving intensity received by the light receiver,
- further comprising detecting the concentration of the discharge solution, based on the light receiving intensity detected by the detection device, and the concentration detection device is corrected before the treatment condition change device sets or changes the treatment conditions as requested.

* * * * *